(12) United States Patent
Priewe et al.

(10) Patent No.: US 11,013,587 B2
(45) Date of Patent: *May 25, 2021

(54) SURGICAL IMPLANT

(71) Applicant: Johnson & Johnson Medical GmbH, Somerville, NJ (US)

(72) Inventors: Jorg Priewe, Kiel (DE); Volker Harms, Hamburg (DE)

(73) Assignee: Johnson & Johnson Medical GMBH, Norderstedt (DE)

( * ) Notice: Subject to any disclaimer, the term of this patent is extended or adjusted under 35 U.S.C. 154(b) by 278 days.

This patent is subject to a terminal disclaimer.

(21) Appl. No.: 15/883,567

(22) Filed: Jan. 30, 2018

(65) Prior Publication Data

US 2018/0161141 A1   Jun. 14, 2018

Related U.S. Application Data

(62) Division of application No. 14/202,513, filed on Mar. 10, 2014, now Pat. No. 9,962,250.

(30) Foreign Application Priority Data

Mar. 11, 2013  (DE) .......................... 102013004574.6

(51) Int. Cl.
    *A61F 2/00*     (2006.01)
    *A61L 15/64*   (2006.01)
(52) U.S. Cl.
    CPC ............ *A61F 2/0063* (2013.01); *A61L 15/64* (2013.01); *A61F 2/0077* (2013.01); *A61F 2250/0031* (2013.01)

(58) Field of Classification Search
    CPC . A61K 47/26; A61K 9/00; A61K 9/70; A61K 9/0021; A61K 9/7007; A61K 9/0014; A61M 37/00; A61M 37/0015; A61M 2037/0023; A61M 2037/0046; B29C 39/026; B29K 2089/00; B29L 2031/7544; B29L 2031/756; A61P 17/02;
    (Continued)

(56) References Cited

U.S. PATENT DOCUMENTS 6,106,558 A      8/2000  Picha
9,839,507 B2 *  12/2017  Harms .................. B29C 43/203
(Continued)

FOREIGN PATENT DOCUMENTS

EP       2476444        7/2012
JP     2010537758 A    12/2010
(Continued)

OTHER PUBLICATIONS

Hern & Aacute, Long-Term Anisotropic Mechanical Response of Surgical Meshes Used to Repair Abdominal Wall Defects, J. Mech Behav Biomed Materi, 2012, pp. 257-271, vol. 5, Issue 1.
(Continued)

*Primary Examiner* — Jeffrey M Wollschlager
*Assistant Examiner* — Armand Melendez

(57) ABSTRACT

A surgical implant (20) comprises a flexible basic structure (22) having a face and a plurality of resorbable film pieces (26) attached to the face of the basic structure (22). Each film piece (26) comprises a plurality of solid protrusions (28) emerging from the respective film piece (26) is a direction away from the basic structure (22).

3 Claims, 8 Drawing Sheets

Figure 1B:
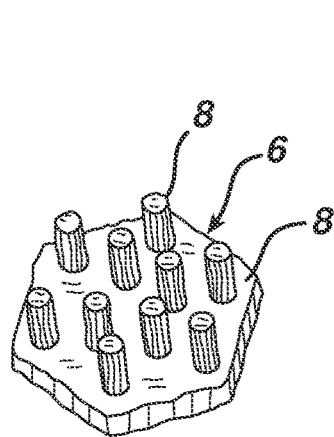

(58) Field of Classification Search
CPC ............ A61F 2/0063; A61F 2250/0031; A61F 2/0077; A61F 2002/30322; A61F 2210/0076; A61F 2220/0008; A61F 2220/0016; A61F 2220/0033; A61F 2250/0026; A61F 2250/003; A61F 2250/0097; A61F 2/02; A61L 27/34; A61L 31/129; A61L 2300/254; A61L 2300/61; A61L 2300/80; A61L 27/50; A61L 27/54; A61L 27/56; A61L 31/10; A61L 31/146; A61L 31/148
See application file for complete search history.

(56) References Cited

U.S. PATENT DOCUMENTS

| | | | |
|---|---|---|---|
| 10,052,184 B2* | 8/2018 | Deichmann | A61F 2/0063 |
| 2002/0077661 A1 | 6/2002 | Saadat | |
| 2003/0208888 A1* | 11/2003 | Fearing | A44B 18/0049 24/442 |
| 2008/0109017 A1 | 5/2008 | Herweck et al. | |
| 2011/0021965 A1* | 1/2011 | Karp | A61L 15/64 602/54 |
| 2018/0235740 A1* | 8/2018 | Deichmann | A61F 2/0063 |

FOREIGN PATENT DOCUMENTS

| | | |
|---|---|---|
| JP | 2015508310 A | 3/2015 |
| JP | 2016514002 A | 5/2016 |
| RU | 121735 U1 | 11/2012 |
| WO | WO 99/45860 | 9/1999 |
| WO | WO 2003/099160 | 12/2003 |
| WO | WO 2006/092236 | 9/2006 |
| WO | WO 2010/093333 | 8/2010 |
| WO | WO 2011/026987 | 3/2011 |
| WO | 2012/007579 A1 | 1/2012 |

OTHER PUBLICATIONS

Sazin, Endoscopic Abdominal Surgery, Endoscopic Abdominal Surgery, 2010, 205-207, c.

Koo, M.Y. et al. "Results from Over One Year of Follow-Up for Absorbable Mesh Insertion in Partial Mastectomy", Yonsei Med Journal, 52(5) pp. 803-808, (2011).

* cited by examiner

SURGICAL IMPLANT

CROSS REFERENCE TO RELATED APPLICATIONS

This application is a divisional application of U.S. patent application Ser. No. 14/202,513 filed Mar. 10, 2014 which claims priority from German Patent Application DE 102013004574.6 filed Mar. 11, 2013 the disclosure of which is hereby incorporated by reference in its entirety.

The invention relates to a surgical implant, in particular to a tissue reinforcing implant for repair of inguinal hernias and/or ventral/incisional hernias.

Hernia repair is one of the most common surgical procedures, with approximately 6.4 million procedures performed globally every year. Approximately 3.1 million hernias (48%) are repaired with flat mesh annually.

The mesh serving as a surgical implant reinforces the area of the hernia. To achieve a safe fixation, the mesh can be sutured to the bodily tissue close to the hernia. However, the suturing step delays the surgical procedure and can cause post-surgical pain to the patient, e.g. due to nerve damage.

WO2003/099160 A discloses a surgical implant comprising a knobbed film which can be connected to a surgical mesh. The knobs are hollow and increase the flexibility of the film. The knobbed film can be produced from a resorbable polymer film using a thermal deforming process. Depending on the design, the knobs may increase or decrease the friction between the implant and the bodily tissue, thus achieving a fixation effect or enhanced mobility, respectively.

EP 2 476 444 A describes a medical device including a porous substrate and a film formed within the pores of the substrate. This device does not exhibit self-fixation properties.

WO 2011/026987 A discloses a prosthetic fabric (mesh) comprising an arrangement of yarns and barbs protruding outwards relative to a face of the fabric. The barbs, which serve as a fixation aid, may be formed from yarns or, as hooks produced from a biocompatible material, are attached to the fabric. The other face of the fabric comprises a microporous layer made of a bio-resorbable material. The barbs are generally sharp due to a cutting process. To decrease the tendency of this product to adhere to itself, e.g. when folded for delivery through a trocar sleeve, the barbs are covered with a coating made of a water-soluble material, which dissolves during the surgical operation. Nevertheless, the handling of the product may be difficult.

WO 99/45860 A describes generally hard biocompatible substrates comprising an array of surface projections of nanometer dimensions, which prevent cells from attachment.

U.S. Pat. No. 6,106,558 discloses a neuro-decompression device utilizing particular surface topographies to disrupt scar tissue formation around nerves. The device comprises protrusions formed in a foamed basis material.

The problem of the invention is to provide a surgical implant, in particular for the repair of hernias, which reduces the need for suturing and can be handled during a surgical procedure in an easy, quick and safe way.

This problem is solved by a surgical implant according to claim 1. Claim 21 is directed to a process of manufacturing such surgical implant. Advantageous embodiments of the invention follow from the dependent claims.

The surgical implant according to the invention comprises a flexible basic structure having a face and a plurality of resorbable film pieces attached to the face of the basic structure. Each film piece comprises a plurality of solid protrusions emerging from the respective film piece in a direction away from the basic structure.

In advantageous embodiments of the invention, the basic structure comprises a mesh-like structure having pores. The term "mesh-like structure" is to be understood rather general and includes a porous flexible sheet in general and more particularly, e.g., meshes (surgical meshes), tapes, perforated films, non-woven fabric, woven fabric, knitted sheets, knitted tapes, braided sheets, braided tapes, collageneous fibrillar sheets, mesh pouches and mesh plugs. In mesh pouches or mesh plugs, a mesh is folded or rolled and optionally fixed to it self at some points or areas, or a corresponding structure is provided from several mesh pieces. Other examples for porous basic structures are foams and sponges.

For example, the basic structure can comprise a surgical mesh having pores, wherein the above face is formed by one side of the surgical mesh. In this case, the implant can be used, e.g., for hernia repair. It is also conceivable to use the surgical implant according to the invention as, e.g., a pelvic mesh or a breast implant. In such cases, the basic structure of the implant is adapted to the desired purpose. Generally, it is not required that resorbable film pieces are attached over the entire face of the mesh-like structure or, more general, of the basic structure.

All the film pieces of the implant may have the same size. In other embodiments, the film pieces have different sizes. Generally, the presence of the film pieces does not significantly affect the flexibility of the basic structure because the film pieces are independent pieces which do not form a continuous layer. In contrast thereto, a surgical implant designed, e.g., as a composite of a surgical mesh and a film layer covering the whole surface of the surgical mesh would be generally stiffer, which could be disadvantageous, depending on the kind of surgery contemplated.

The protrusions provide to the surgical implant self-fixating properties on biological soft tissue. They mechanically grip into the soft tissue, which re suits in enhanced resistance to shear forces as well as peel forces, an particular at the protrusions are solid. Generally, there is no need for securing the implant additionally by sutures, which decreases the risk of injury and pain to the patient and facilitates the surgical procedure and reduces the time needed therefore. Nevertheless, if required, additional sutures might be applied.

In advantageous embodiments of the inventions, at least one protrusion is rod-like, pillar-like or mushroom-shaped. A shape defined by a respective body and a respective head, the body emerging from the film piece and terminating in the head, and the head projecting laterally with respect to the body, is a kind of mushroom shape, but somewhat more general. Such mushroom-like protrusions can exhibit a particular effective self-fixation effect. Here and in the following, the term "at least one" includes embodiments in which there are many protrusions on the surgical implant and/or in which all protrusions have the same shape. Of course, the implant might also comprise protrusions of different shapes or sizes or protrusions provided in different area densities on respective film pieces.

Preferably, at least one film piece comprises a protrusion having a longitudinal axis which emerges from the film piece at an angle relative to the surface of the film piece in the range of from 50° to 90° or in the range of from 70° to 90°.

The protrusions may have a large variety in dimensions. For example, at least one protrusion can have a length, measured along a longitudinal axis of the protrusion, in the range of from 20 μm to 5000 μm or in the range of from 100 μm to 500 μm or of from 20 μm to 400 μm.

If the total area of all film pieces is not too large, the flexibility of the basic structure is not much decreased by the presence of the film pieces. In advantageous embodiments, 10% to 50% of the area of the face of the basic structure are covered by film pieces, which also discloses all intermediate values in this range.

On the other hand, if the total area of all film pieces comprising protrusions is not too small, the desired self-fixation effect will be achieved. The optimum area also depends on the properties of the protrusions and the biological tissue in question. Generally, an area of greater than 5% of the area of the face of the basic structure might already be sufficient.

In advantageous embodiments of the invention, the basic structure comprises a mesh-like structure having pores, as already mentioned before. In this case, at least one film piece may have a size being equal to or greater than the size of a pore of the mesh-like structure. For example, 90% of the film pieces could have a size greater than the mesh pores. It is not required that the circumference line of a particular film piece coincides with the lines defined by the material of the mesh. For example, the film pieces may be designed as strips or crosses which, e.g., cover a crossing point of the mesh-like structure, or just do not cover a crossing point but are attached to other lines of the mesh structure. If the pores of the mesh-like structure are large enough, it is also conceivable that a film piece has a size smaller than the size of a pore of the mesh-like structure.

A mesh-like basic structure is preferably macro-porous with typical pore dimensions of greater than 0.5 mm, which supports good tissue integration. Other pore sizes are conceivable as well, however. As already indicated above, a mesh or mesh-like basic structure can be provided in any kind known in the art, e.g., warp-knitted or weft-knitted or crochet-knitted or woven. A design as perforated film or foil is also conceivable. Any filaments of the mesh may be bio-absorbable or non-absorbable, depending on the material. Thus, the mesh can be absorbable (resorbable), non-absorbable or partially absorbable. The filaments can be designed as mono-filaments or as multi-filaments. Tape yarns and drawn film tapes are conceivable as well. Any blends, mixtures or composites of materials and designs are also possible. Moreover, the filaments can be coated. A mesh designed as a perforated sheet is conceivable as well. Generally, the mesh-like structure is flexible and has an a real basic shape. For example, it can be based on a commercially available hernia repair mesh.

Preferably, the film pieces are arranged in a regular pattern. Examples are a centric pattern (in which the film pieces are arranged in one or more than one concentric rings about a common center) or, if the basic structure comprises a mesh, in an inverted grid or inverted mesh pattern (in which the film pieces follow the mesh pattern and have sizes in the order of one or more than one mesh-pore).

The film pieces can be provided in a large variety of shapes (e.g., as hexagon, rounded hexagon, triangle, rounded triangle, rectangle, rounded rectangle, square, rounded square, circle, ellipse, or cross-shaped, snake-like, spiral-like, etc.) and sizes (e.g. with a typical length or width dimension in the range of from 0.7 mm to 50 mm or of from 2 mm to 5 nm). The variety in patterns has already been mentioned above and can be extended to irregular patterns as well.

Typically (but not exclusively), each film piece is surrounded by an area of the basic structure free from other film pieces, wherein this area has a width, e.g., in the range of from 1 mm to 50 mm or in the range of from 1 mm to 9 mm. However, it is also conceivable that film pieces touch each other.

Moreover, film pieces may be connected to each other via struts, e.g. in pairs (e.g. with one strut between the members of the pair), in small groups or in larger groups. Such struts can be made from the same material as the film pieces. If the struts are relatively narrow, they will form connectors which are not stiff and do not deteriorate the flexibility behavior of the implant.

The film pieces can have a thickness, e.g., in the range of from 5 μm to 250 μm, or in the range of from 10 μm to 200 μm. This is the thickness of the film in an area between protrusions. Generally, the thickness may vary and can be significantly smaller than the thickness of an originally flat film layer used to produce the film pieces including protrusions (see below for examples) because, during the production process, part of the material of the original film layer can be transferred to the protrusions.

Preferably, the film pieces and the respective protrusions are made in one piece, see below for examples of manufacturing processes.

If the basic structure comprises a mesh-like structure having the face and an opposite face and comprising pores, a film can also be attached to the opposite face. This film may have a variety of properties. For example, it may be provided as single piece, e.g. as a contiguous film covering part of or the whole opposite face of the mesh-like structure. Or it may be provided as a plurality of film pieces, similar to the film pieces at the face. Moreover, the film at the opposite face may be resorbable or non-resorbable. It may comprise protrusions in order to achieve a self-fixation effect, or it may be more or less smooth, without protrusions. If the film has barrier properties, bodily tissue can be prevented from growing into the pores of the mesh-like structure.

In another advantageous embodiment of the invention, the effect of film pieces provided with protrusions on both sides (face and opposite face) of the basic structure is achieved by one layer of film pieces. In this case, the basic structure is mesh-like and the film pieces extend into the mesh pores present in the basic structure, wherein protrusions emerge from the film pieces in both directions, away from the face of the basic structure and away from the opposite face of the basic structure. An example of a manufacturing process for such implant is presented further below.

The film pieces are resorbable because some time after the surgical operation, the self-fixation effect is not needed anymore. If the film pieces have disintegrated or have been absorbed at that time, tissue growth at the basic structure and the healing process may be improved if the basic structure is also resorbable, preferably the film pieces are faster resorbable than the basic structure.

Suitable materials for the resorbable film pieces are well known in the art. The selection of the film material depends, e.g., on the resorption period. Considering processes of manufacturing the implant according to the invention, it may also depend on the melting temperature of the film material relative to that of the material of the basic structure (see below). For example, the film pieces may comprise poly-p-dioxanone ("PDS"), copolymers of glycolide and ε-caprolactone (e.g., "Monocryl" of Johnson & Johnson Medical GmbH) and/or copolymers of glycolide and lactide (in particular in the ratio 90:10, "Vicryl" of Johnson & Johnson Medical GmbH.). Generally, a large variety of synthetic bioabsorbable polymer materials can be used, for example polyhydroxy acids (e.g., polylactides, polyglycolides, polyhydroxybutyrates, polyhydroxyvaleriates), copolymers of lactide and trimethylene carbonate, copolymers of glycolide, lactide and trimethylene carbonate, polycaprolactones, polydioxanones, synthetic (but also natural) oligo- and polyamino acids, polyphosphazenes, polyanhydrides, polyorthoesters, polyphosphates, polyphosphonates, polyalcohols, polysaccharides, polyethers. However, naturally occurring materials such as collagens and gelatine or naturally derived materials such as bioabsorbable gel films cross-linked with omega 3 fatty acids or oxygenized regenerated cellulose (ORC) are conceivable as well.

Suitable materials for the basic structure are also well known in the art. Non-resorbable or very slowly resorbable substances include, e.g., polyalkenes (e.g. polypropylene or polyethylene), fluorinated polyolefins (e.g. polytetrafluoroethylene (PTFE) or polyvinylidene fluoride), polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimides as well as mixtures and/or co-polymers of these substances. Other advantageous materials, many of them being resorbable, include polyhydroxy acids, polylactides, polyglycolides, copolymers of lactide and trimethylene carbonate, copolymers of glycolide, lactide and trimethylene carbonate, polyhydroxybutyrates, polyhydroxyvaleriates, polycaprolactones, polydioxanones, polyp-dioxanone, synthetic and natural oligo- and polyamino acids, polyphosphazenes, polyanhydrides, polyorthoesters, polyphosphates, polyphosphonates, rivlyaicohols, polysaccharides, polyethers, cellulose, bacterial cellulose, polyamides, aliphatic polyesters, aromatic polyesters, copolymers of polymerizable substances thereof, resorbable glasses. Particularly advantageous materials include polypropylene (non-resorbable), blends of polyvinylidene fluoride and copolymers of vinylidene fluoride and hexafluoropropene (nonabsorbable, e.g. "Pronova" of Johnson & Johnson Medical GmbH) PTFE (non-resorbable; including ePTFE and cPTFE), polysilicones (non-resorbable), poly-p-dioxanone ("PDS", resorbable)), copolymers of glycolide and lactide (resorbable), in particular copolymers of glycolide and lactide in the ratio 90:10 ("Vicryl", resorbable), copolymers of glycolide and ε-caprolactone ("Monocryl", resorbable). Biologic materials such as allograft and xenograft are conceivable as well.

In summary, the surgical implant according to the invention has a plurality of advantages. The self-fixation properties result in a better comfort to the patient due to a reduced risk of chronic pain that may be associated with suture fixation. The basic structure, e.g. a surgical mesh, is securely held in place during the tissue integration period so that mesh migration is prevented. Afterwards, the film pieces including the protrusions may be absorbed.

Moreover, the time efficiency during the surgical operation is improved. In particular, the surgical implant can be easily prepared and handled intra-operatively. Generally, because of the design of the protrusions, the implant does not tend to adhere to itself when in a rolled or folded state. Thus, the implant is well suitable for laparoscopic placement. It can be forwarded to the site of surgery through a trocar sleeve and easily be unrolled or unfolded thereafter, without sticking to itself. Moreover, although the implant is self-fixating, it allows for repositioning as it is generally possible to peel the implant off from bodily tissue and position it again at a different or displaced location. Since it is generally not required to fix the implant by sutures, the surgical procedure tends to be shorter. If nevertheless desired, the implant can be additionally fixated by, e.g., suturing.

Prior art films or self-fixating films connected to a surgical mesh may impart stiffness which reduces the conformity to anatomical structures and also reduces the number of attachment points at an uneven tissue structure. In contrast thereto, the surgical implant according to the invention largely preserves the flexibility and elasticity of the basic structure and conforms well, and at the same time sticks well to anatomical structures even if these are not plan.

If the surgical implant is designed as a soft-tissue implant, e.g. a hernia implant, and is adapted to fix itself at least partially in soft tissue such as muscle or fat, the friction between the surgical implant and the soft tissue can be increased in at least one direction (measured essentially in the plane of the implant) by a factor of 2 or more, compared to a corresponding implant without protrusions.

In a particularly advantageous embodiment, the surgical implant according to the invention comprises a basic structure designed as a long-term stable soft-tissue repair mesh comprising pores having a size of at least 1 mm, and the total area of all film pieces is less than 25% of the area of the face of the basic structure. The protrusions are mushroom shaped, are made in one piece with the respective film pieces and have a length, measured along a longitudinal axis of the respective protrusion, in the range of from 300 µm to 500 µm. Optionally, additional film pieces with protrusions can be provided on the opposite side of the mesh.

A surgical implant according to the invention may be manufactured by using the following steps: providing a mold containing an array of cavities, each cavity having the shape of one protrusion; filling the mould with a fluid material forming the film pieces and the protrusions according to a pattern defining the shapes and locations of the film pieces; hardening the fluid material; attaching the film pieces to a basic structure, with the protrusions pointing away from the basic structure; removing the mold.

The order of how these steps are listed above does not necessarily represent the sequence in which the steps are executed when the process of manufacturing according to the invention is performed, which is explained in more detail further below.

The mold is preferably flexible and comprises, e.g., silicone, polyurethane, a natural rubber or a synthetic rubber. Silicone, e.g., is very flexible and thermo-stable. The mold is basically planar and provides a surface for forming the film pieces. Extending from this surface, there are cavities, each one having the shape of one protrusion. A silicone mold, e.g., can be manufactured, e.g., by using a mechanically produced master (a positive of the array of protrusions) of a metal or a polymer as a master mold, which is filled with silicone precursors and reacted. Due to the large elasticity of silicone, the master mold can be removed after the reaction is finished, and in use of the mold the mold can be separated from the protrusions formed by the mold, even in case of laterally projecting parts of the protrusions.

In advantageous embodiments of the process, the pattern defining the shapes and locations of the film pieces is determined by a mask placed between the basic structure and the material to be filled in the mold.

The steps of filling the mold with a fluid material which forms film pieces including the protrusions, of hardening the fluid material and of attaching the film pieces to a basic structure, in particular a surgical mesh, may be performed essentially at the same time, for example in the following way:

In this advantageous embodiment, the process uses a layered assembly comprising, in this order: the mold, a surgical mesh (e.g. of polypropylene) as the basic structure, the mask, a sheet of material (e.g. of poly-p-dioxanone) for the film pieces having a lower melting point than the surgical mesh, and a flexible plate device having a closed surface. The sheet of material is heated to a temperature being higher than its melting point and lower than the melting point of the surgical mesh so that the sheet becomes fluid. Then the mold and the plate device are pressed towards each other, the plate device serving as a counter-part or kind of anvil, whereby the material for the film pieces is transferred through the mask into the mold and, at the same time, embeds the surgical mesh. After decreasing the temperature, the fluid material solidifies (which is the hardening step mentioned above) so that the mold can be removed, due to its high elastcity. In this way, the film pieces are shaped by the mask and firmly connected to the surgical mesh, and the protrusions are formed, all steps occurring virtually simultaneously.

In a variant of the latter embodiment, the initial positions of the surgical mesh and the sheet of material for the film pieces are interchanged. In this case, the material for the film pieces is transferred into the mold and embedded in the surgical mesh in those areas which are not shielded by the mask.

The flexible plate device can comprise a closed surface. Alternatively, it may be designed as a second mold, which is flexible and contains an array of cavities, each cavity having the shape of one protrusion. This second mold is similar to the other mold and can be used to prepare protrusions on the opposite face of the mesh to produce a surgical mesh implant comprising protrusions on both faces.

Depending on the materials used and the details of the process, the hardening step may be performed by evaporation of a solvent, by cooling (as in the examples above) or by reacting reactants forming the film and the protrusions.

In the following, some aspects of the invention are further disclosed in general terms.

EXAMPLES OF APPLICATIONS

Soft tissue repair implants such as surgical meshes are mainly used when a defect or weakness exists in soft tissue or a tissue hole has to be filled or covered:

(a) Ventral and inguinal hernias occur when a tissue, a structure, or part of an organ protrudes through an abnormal opening in the body. It is most commonly associated with the projection of the intestine through a weak point in the abdominal wall. Hernia repair devices could be made in different shapes and from different materials, in the form of flat devices, basically flat but curved devices, pouches, bags or folded into plugs.

(b) Surgical meshes, tapes or slings are used in the field of pelvic disorders like stress urinary incontinence or pelvic organ prolaps. In these applications, there may be a need to place the fabric in contact with the vaginal wall (e.g., a pelvic mesh) or in contact with the urethra such as with the GYNECARE® TVT system from Ethicon, Inc., wherein the inventive assembly might support the locking in certain regions of the tape or mesh.

(c) Durapatches are used after brain surgery to cover and close the dura mata. The dura mater is the tough, inflexible fibrous sheath, which is the outermost of three layers that surround the brain and spinal cord. Commercial grafts are made up of either biologic (includes xenografts and allografts) or synthetic material. The inventive micro-protruded film patches in certain areas on one of the both sides might help to keep the implant in place.

(d) Rotator cuff reinforcement grafts are most often used in cases where existing tissue can no longer be used or treated to support the rotator cuffs functions.

(e) Absorbable pouches are used in the field of trauma surgery as a liver compression device to reduce bleeding, like "Vicryl Mesh bag A".

(f) Grafts in the field of breast reconstruction are used with the "TRAM-flap" procedure, where an autogeneous tissue reconstruction of the breast is performed with the transverse rectus abdominus myocutaneous (TRAM) flap from the chest. The abdominal wall donor site for the muscle flap might develop a potential abdominal wail weakness, bulging, and hernia. To prevent hernia, most surgeons will use a synthetic mesh when closing the abdomen. Fabrics such as absorbable meshes like "Vicryl" mesh or "TiGr matrix" are also used in breast augmentation or reconstruction i.e. in oncoplastic surgery which is defined as a combination of tumor excision, with appropriate margin including lympectomy or mastectomy, and immediate reconstruction of the breast (Koo et al. 2011 "Results from Over One Year of Follow-Up for Absorbable Mesh Insertion in Partial Mastectomy "Yonsei Med J 52(5):803-808, 2011). The inventive device will help to minimize sutures, tacks or glues.

(g) Soft tissue repair devices are used as a filler, to bulk tissue e.g. in cosmetic surgery to remove wrinkles or in fistula surgery to fill the fistula channels. Depending on the intended use, absorbable materials might be used.

Film Piece Size and Shape

Film pieces are preferably in the millimeter range of 1 mm-10 mm, not introducing much stiffness to the basic structure and having a thickness of 5 µm-500 µm. The film pieces can have any shape, e.g. circle, oval, triangle, rectangle, square, pentagon, hexagon, cross, star.

The film-piece stiffness, shape, and overall thickness, and the film piece edges could be used, additionally to the microprotrusions, to impart additional features like palpatetibility to give orientation.

Film Piece Pattern and Spacing

Depending on the intended implant use, the film pieces might be arranged peripherally, centrally, or over the whole area. Preferably the total film area, compared to the implant face area, is less than 50%, particularly less than 25% for the total area pattern. For implants having only a central-area or peripheral film pattern, the total film area might be further reduced to geometric considerations. The film piece pattern could be used to adjust parameters like bending stiffness in different directions. Preferably the film piece pattern does not impart much stiffness to the implant to allow conformability also with uneven structures or does not negatively impact features like rolling and unrolling or folding and unfolding during laparoscopic surgery.

Film Piece Connection to Basic Structure

The film pieces can be connected to each other, in the case of a sandwich placement, and/or to the basic structure in a variety of different conventional ways, e.g., sewn, embroidered, bonded (including by thermal means), or welded thermally including ultrasonically. The welding techniques also include, in a broader sense, thermal deformation of at least one of the films (below the melting point of the film). An absorbable melt glue such as polydioxanone as a relatively low melting bioabsorbable polymer might be used as a gluing member for other film piece materials. Other soluble polymers such as polylactide, polycaprolactone or copolymers thereof might be used as solvent glues. Reactive glues like cyanoacrylates or isocyanates or oxiranes may also be used, if biocompatible.

Particularly preferred is a one-step process of microprotrusion generation and connection to a porous tissue repair structure ((basic structure). In the case of large-pore meshes, the film pieces are extending preferably over at least one part of the pore edge.

The micro-protruded film pieces are preferably enveloping/surrounding the basic structure at least in part. This helps to attach the film piece members even to low-attaching surfaces like PTFE or Polypropylene without any surface pretreatment.

Film Piece Micro-Protrusions

The micro-protrusions are solid and preferably in the range of 20 μm to 800 μm, preferably 50 μm-500 μm, particular preferably 250 μm-350 μm, out of the film piece area.

The micro-protrusions alter the attachment to mammalian or human soft tissue during implant placement and or ingrowths.

Micro-protrusions are protruding preferably 45°-90° from the surface of the film pieces and could have a complex structure, like mushroom, curved rod, etc.

Preferred micro-mushrooms with a density of about 288 protrusions per cm of film piece area were prepared. For example, mushrooms were determined by scanning electron microscopy having a height of 288 μm, a foot thickness of 410 μm diameter, a narrowed middle section of 177 μm diameter, and a head section of 410 μm diameter with a rim thickness of the mushroom head of about 12 μm.

Active Ingredients

For example, it may be advantageous to provide an implant of the present invention that has at least one biologically active or therapeutic ingredient which can optionally be released locally after the implantation. Substances which are suitable as active or therapeutic agents may be naturally occurring or synthetic, and include and are not limited to, for example, antibiotics, antimicrobials, antibacterials, antiseptics, chemotherapeutics, cytostatics, metastasis inhibitors, antidiabetics, antimycotics, gynecological agents, urological agents, anti-allergic agents, sexual hormones, sexual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, cells occurring naturally in the body or genetically modified cells. The active or therapeutic agent may be present in various forms including in an encapsulated form or in an adsorbed form. With such active agents, the patient outcome may be improved or a therapeutic effect may be provided (e.g., better wound healing, or inflammation inhibition or reduction).

One preferred class of active agents is antibiotics that include such agents as gentamicin or ZEVTERA™ (ceftobiprole medocaril) brand antibiotic (available from Basilea Pharmaceutica Ltd., Basel Switzerland). Other active agents that may be used are highly effective, broad-band antimcrobials against different bacteria and yeast (even in the presence of bodily liquids) such as octenidine, octenidine dihydrochloride (available as active ingredient in Octeniseptg, disinfectant from Schülke & Mayer, Norderstedt, Germany), polyhexamethylene biguanide (PHMB) (available as active ingredient in Lavasept® from Braun, Switzerland), triclosan, copper (Cu), silver (Ag), nanosilver, gold (Au), selenium (Se), gallium (Ga), taurolidine, N-chlorotaurine, alcohol-based, antiseptics such as Listerine (R) mouthwash, N a-lauryl-L-arginine ethyl ester (LAE), myristamidopropyl dimethylamine (MAPD, available as an active ingredient in SCHERCODINE™ M), oleamidopropyl dimethylamine (OAPD, available as an active ingredient in SCHERCODINE™ O), and stearamidopropyl dimethylamine (SAPD, available as an active ingredient in SCHERCODINE™ S), fatty acid monoesters, and most preferably octenidine dihydrochloride (hereinafter referred to as octenidine), Taurolidine, and PHMB.

One preferred class of active agents are local anesthetics that includes such agents as: Ambucaine, Benzocaine, Butacaine, Procaine/Benzocaine, Chloroprocaine, Cocaine, Cyclomethycaine, Dimethocaine/Larocaine, Etidocaine, Hydroxyprocaine, Hexylcaine, Isobucaine, Paraethoxycaine, Piperocaine, Procainamide, Propoxycaine, Procaine/Novocaine, Proparacaine, Tetracaine/Amethocaine, Lidocaine, Articaine, Bupivacaine, Dibucaine, Cinchocaine/Dibucaine, Etidocaine, Levpbupivacaine, Lidocaine/Lignocaine, Mepivacaine, Metabutoxycaine, Piridocaine, Prilocaine, Propoxycaine, Pyrrocaine, Ropivacaine, Tetracaine, Trimecaine, Tolycaine, combinations thereof, e.g., Lidocaine/prilocaine (EMLA) or naturally derived local anesthetics including Saxitoxin, Tetrodotoxin, Menthol, Eugenol and pro-drugs or derivatives thereof.

Additionally, a contrast agent may be incorporated into the devices of the present invention. Such a contrast agent may be a gas or gas creating substance for ultrasound contrast or MRI contrast, such as metal complexes like GdDTPA or superparamagnetic nanoparticies (Resovis™ or Endorem™) as taught in EP 1 324 783 B1, which is incorporated by reference. X-Ray visible substances might be included as shown in the EP 1 251 794 B1 (incorporated by reference) including pure zirconium dioxide, stabilized zirconium dioxide, zirconium nitride, zirconium carbide, tantalum, tantalum pentoxide, barium sulphate, silver, silver iodide, gold, platinum, palladium, iridium, copper, ferric oxides, not very magnetic implant steels, non-magnetic implant steels, titanium, alkali iodides, iodated aromatics, iodated aliphatics, iodated oligomers, iodated polymers, alloys of substances thereof capable of being alloyed. The contrast agents may be included in or on a mesh, or in or on the film pieces.

Basic Structure

Depending upon the intended use of the tissue repair device, a biocompatible long-term-stable polymer may be used to manufacture the soft-tissue repair member (basic structure). By a long-term-stable polymer is meant a non-resorbable biocompatible polymer, or a bioabsorbable polymer which absorbs or degrades slowly, for example which possesses at least 50% of its original tearing strength in vivo 60 days after implantation. The latter group includes substances such as polyamides, which generally are regarded as resistant, as they are not designed as resorbable materials, but are attacked over time by body tissue and tissue fluids. Preferred materials for the fabric repair member include polyhydroxy acids, polylactides, polypolyhydroxy butyrates, polyhydroxy valeriates, polycaprolactones, polydioxanones, synthetic and natural oligo- and polyamino acids, polyphosphazenes, polyanhydrides, polyorthoesters, polyphosphates, polyphosphonates, polyalcohols, polysaccharides, polyethers, cellulose, bacterial cellulose, polyamides, aliphatic polyesters, aromatic polyesters, copolymers of polymerizable substances thereof, resorbable glasses. Particularly preferred materials for the fabric repair member include polypropylene and mixtures of polyvinylidene fluoride and copolymers of vinylidene fluoride and hexafluoropropene, PTFE, ePTFE, and cPTFE, silicone, but other conventional biocompatible materials are also useful. The fabric repair members may be constructed from monofilaments, multifilaments, or combinations thereof. The fabric repair member may contain, in addition to a long-term stable polymer, a resorbable polymer (i.e., bioabsorbable or biodegradable). The resorbable and the long-term stable polymer preferably contain monofilaments and/or multifilaments. The terms resorbable polymers and bioabsorbable polymers can be used synonymously. The term bioabsorbable is defined to have its conventional meaning.

If only short-time tissue support is needed, like for fistula plugs, the fabric repair member may be manufactured from a bioabsorbable polymer or bioabsorbable polymers without any long-term-stable polymers.

Optionally the basic structure might be prepared from a biologic material such as allograft, xenograft.

Additional Layer or Layers

Tissue repair or reinforcing implants, such as meshes, may be designed to enable tissue in-growth on one side (e.g., by having open pores or interstices) and resist tissue ingrowth on the opposing side (e.g., by having a smooth surface such as a film or non-porous layer, conventionally referred to in the art as an adhesion barrier). This is important when the mesh implants are used or implanted in the abdominal area, for example in hernia repair procedures, where adhesion of the per (i.e., tissue ingrowth) to the implant is desired while tissue ingrowth or adhesions on the visceral side is unwanted (i.e., anti-adhesion). Several conventional products are known in the art and commercially available having one basically smooth side which is an adhesion barrier and one porous or rough side for tissue in-growth. The products may be completely absorbable, completely non-absorbable, or partially absorbable and partially non-absorbable. The products may be composites of multiple mesh layers and adhesion resistant barriers. Certain implants are ready for use out of the package (e.g., Proceed® Hernia Mesh, PhysioMesh®; Gore DualMesh®, and Bard Composix® Mesh) and other mesh implants are required to be pre-soaked for several minutes in water or saline solution prior to implantation in order to swell the adhesion barrier and make the implant sufficiently soft for implantation and placement in the patient (e.g., Sepramesh Parietex® Composite).

Additional layer/layers might be added to the surgical implant either between multiple-protruded film pieces and the basic structure or on the opposite side, or on both locations, which would result in the following assemblies: film pieces+additional layer+basic structure or film pieces+basic structure+additional layer or film pieces+additional layer+basic structure+additional layer.

The additional layer or layers could have different effects on the tissue repair implant like imparting stiffness or improving tissue regeneration or ingrowth.

The additional layers that are used to manufacture the tissue repair implant devices of the present invention should have a thickness that is sufficient to effectively prevent adhesions from forming. The thickness will typically range from about 1 µm to about 500 µm, and preferably from about 5 µm to about 50 µm. The films suitable for use as the first or optional second films of the tissue repair devices of the present invention include both bioabsorbable and non-absorbable films. The films are preferably polymer-based and may be made from various conventional biocompatible polymers. Non-resorbable or very slowly resorbable substances include polyalkenes (e.g. polypropylene or polyethylene), fluorinated polyolefins (e.g. polytetrafluoroethylene or polyvinylidene fluoride), polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimades as well as mixtures and/or co-polymers of these substances. Also useful are synthetic bioabsorbable polymer materials, for example polyhydroxy acids (e.g. polylactides, polyglycolides, polyhydroxybutyrates, polyhydroxyvaleriates), polycaprolactones, polydioxanones, synthetic and natural oligo- and polyamino acids, polyphosphazenes, polyanhydrides, polyorthoesters, polyphosphates, polyphosphonates, polyalcohols, polysaccharides, polyethers. However, naturally occurring materials such as collagens, gelatin or natural-derived materials such as bioabsorbable omega3-fatty-acid-crosslinked gel films or oxygenized regenerated cellulose (ORC) can also be used.

The films used in the tissue repair devices of the present invention may cover the entire outer surfaces of the repair fabric member (basic structure) or a part thereof. In some cases, it is beneficial to have films overlapping the borders of the repair fabric. The term border used herein means a peripheral edge or central edge if there is a hole in the mesh, e.g., for receiving an anatomical structure like the bowel for treating or preventing parastomal hernia or the spermic cord.

The films may be perforated before or after assembling the device, or the films may be manufactured in such a manner that they contain pores. However, it will be appreciated by those skilled in the art that precautions have to be taken to prevent damage to the fabric member or the second film when perforating an assembled device.

The films can be joined together in various conventional manners, for example by sewing, gluing, welding, and laminating. The joining/connection can be about the periphery, in the center region, or over the whole assembly as a point linear or overall connection, making sure that the pores of the top and bottom films are substantially offset.

The films can be connected to each other and/or to the repair fabric member (basic structure) in variety of different conventional ways, e.g., sewn, embroidered, bonded (including by thermal means) in partial regions (e.g., in points or along lines or strips, such as the peripheral edge), or welded thermally including ultrasonically. The welding techniques also include, in the wider sense, thermal deformation of at least one of the films (below the melting point of one film). The implant can optionally have embroidered structures designed as reinforcements, e.g. rib-like structures.

Particularly preferred for the devices of the present invention is a film-to-film connection using heat lamination techniques, optionally by using an additional biocompatible melt glue such as polydioxanone as a relatively low-melting bioabsorbable polymer. Other soluble polymers such as polylactide, polycaprolactone or copolymers thereof might be used as solvent glues. Reactive glues like cyanoacrylates or isocyanantes or oxiranes may also be used if biocompatible.

In the following, the invention is further explained by means of embodiments. The drawings show in.

Figure 1A:
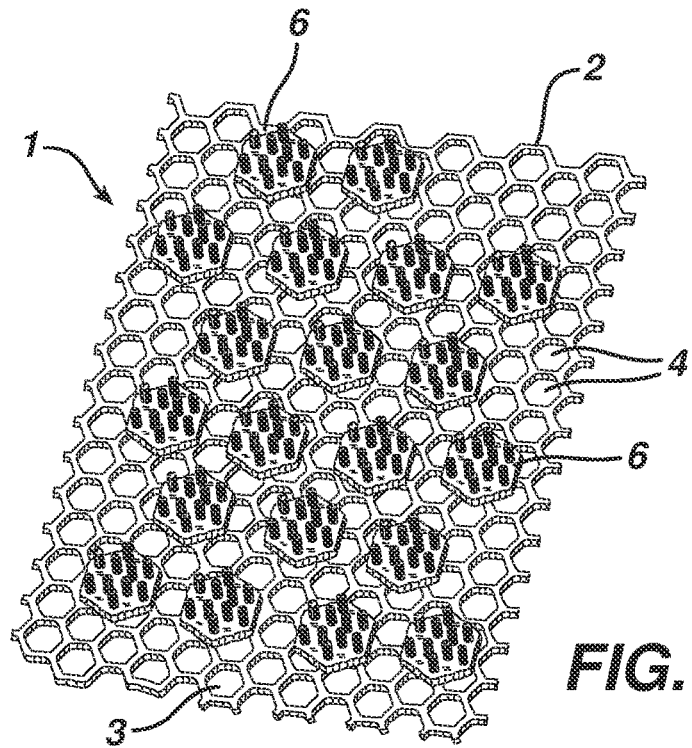
Figure 2:
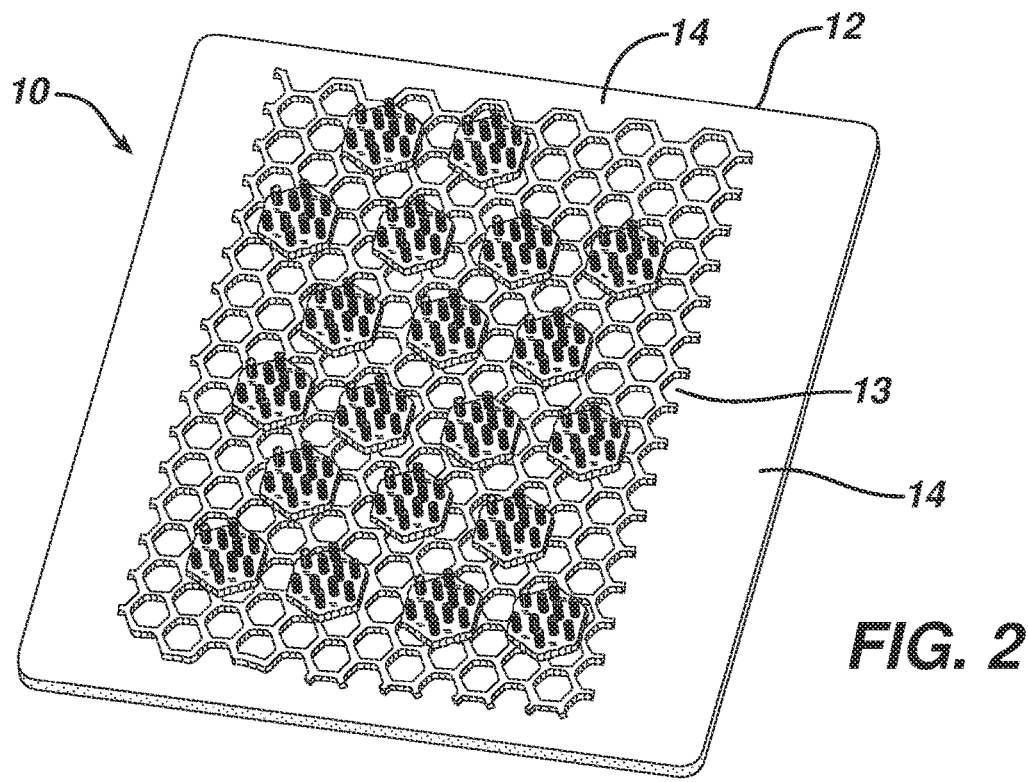
Figure 6A:
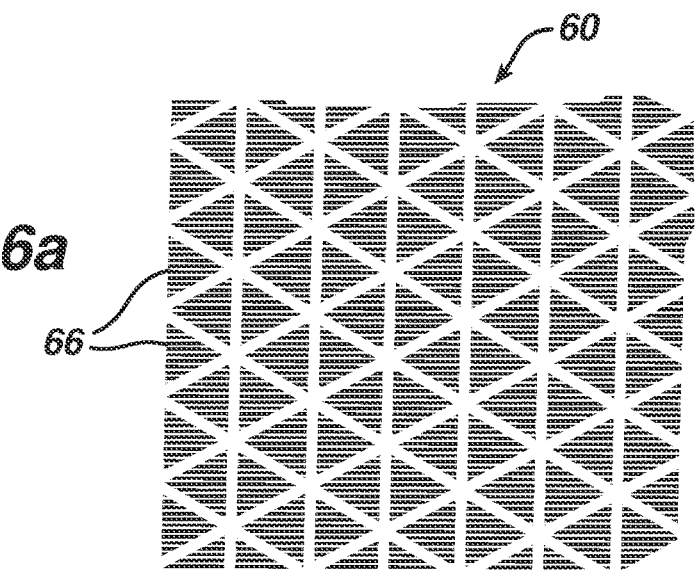
Figure 6B:
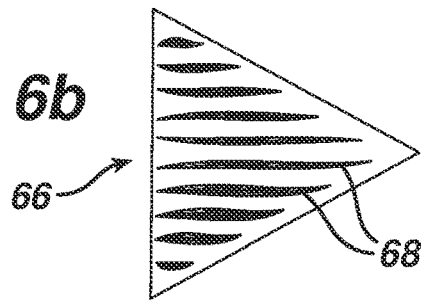
Figure 6C:
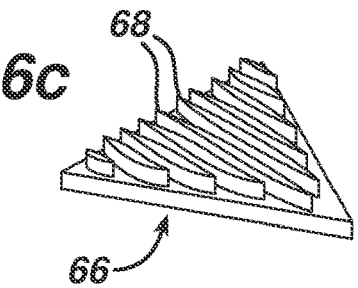
Figure 7:
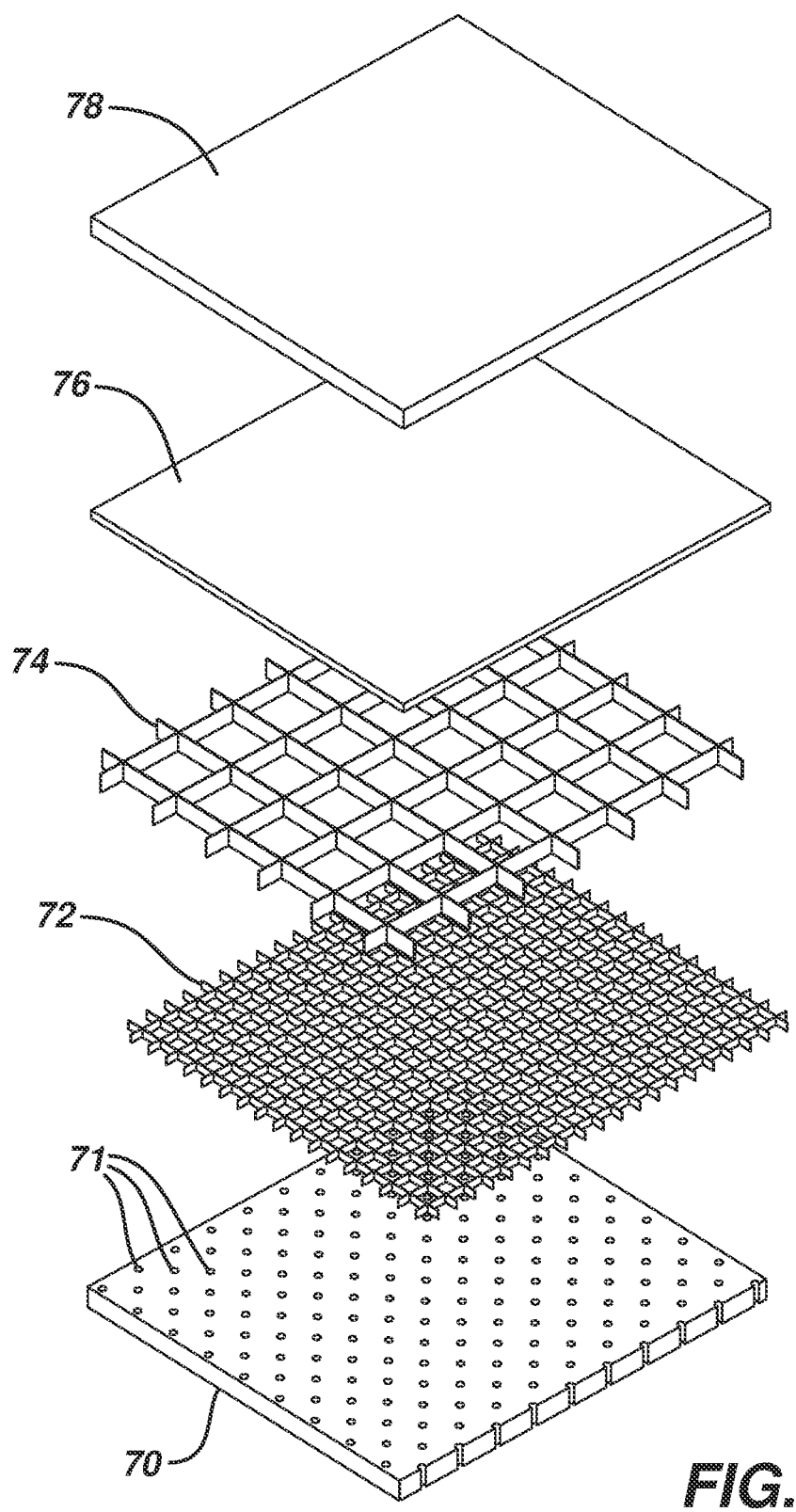
Figure 8:
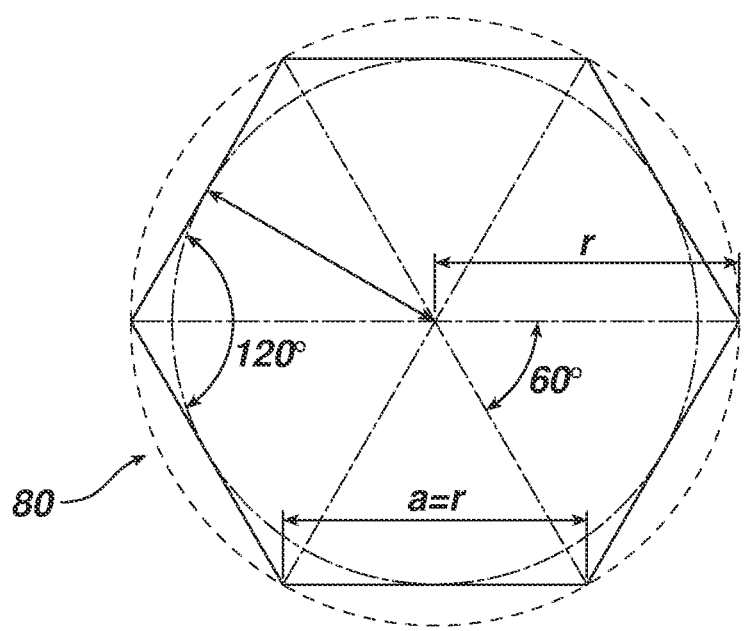
Figure 9:
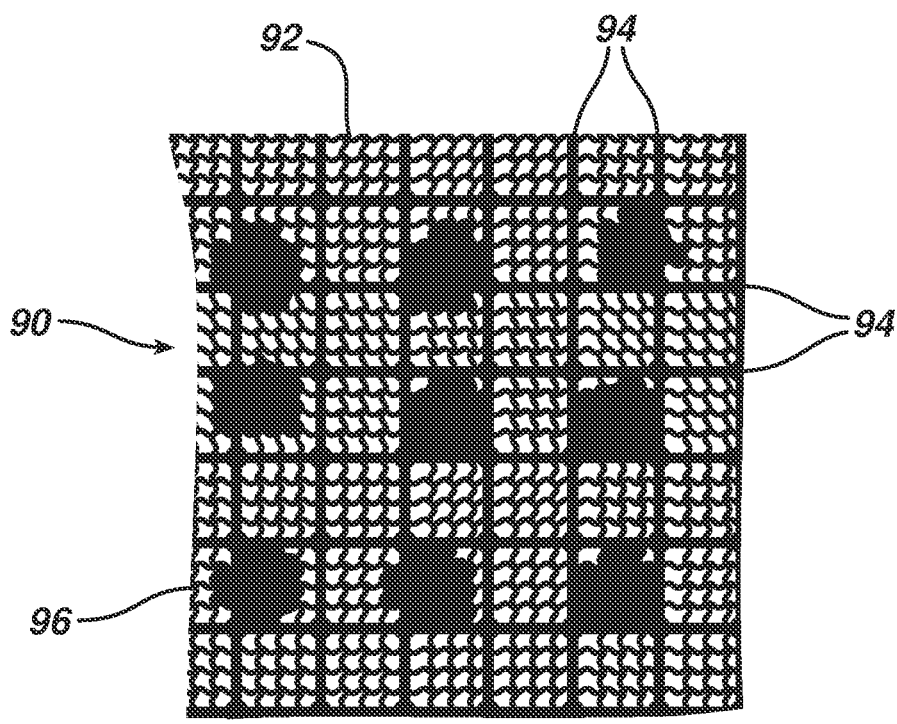
Figure 10:
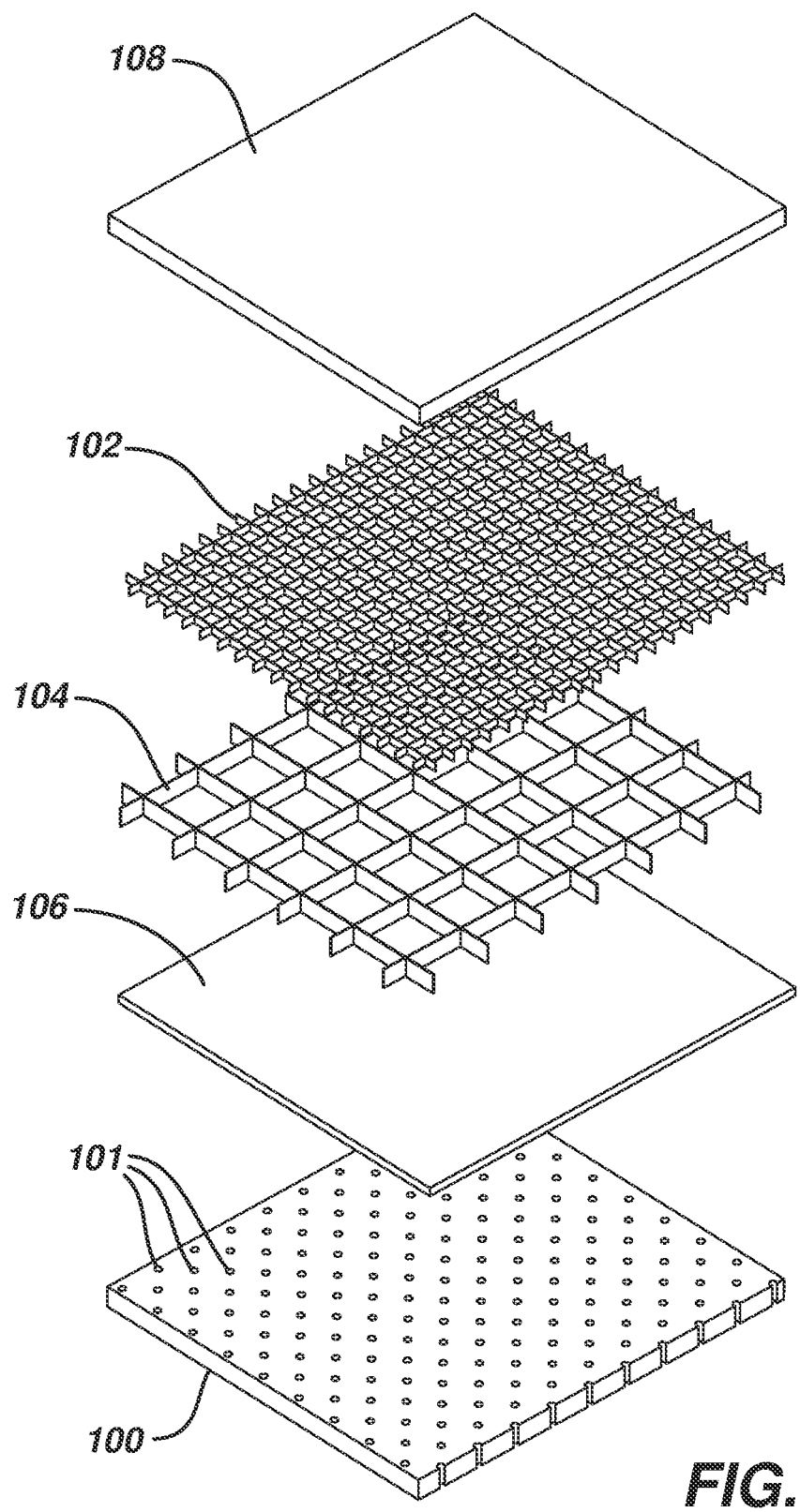
Figure 11:
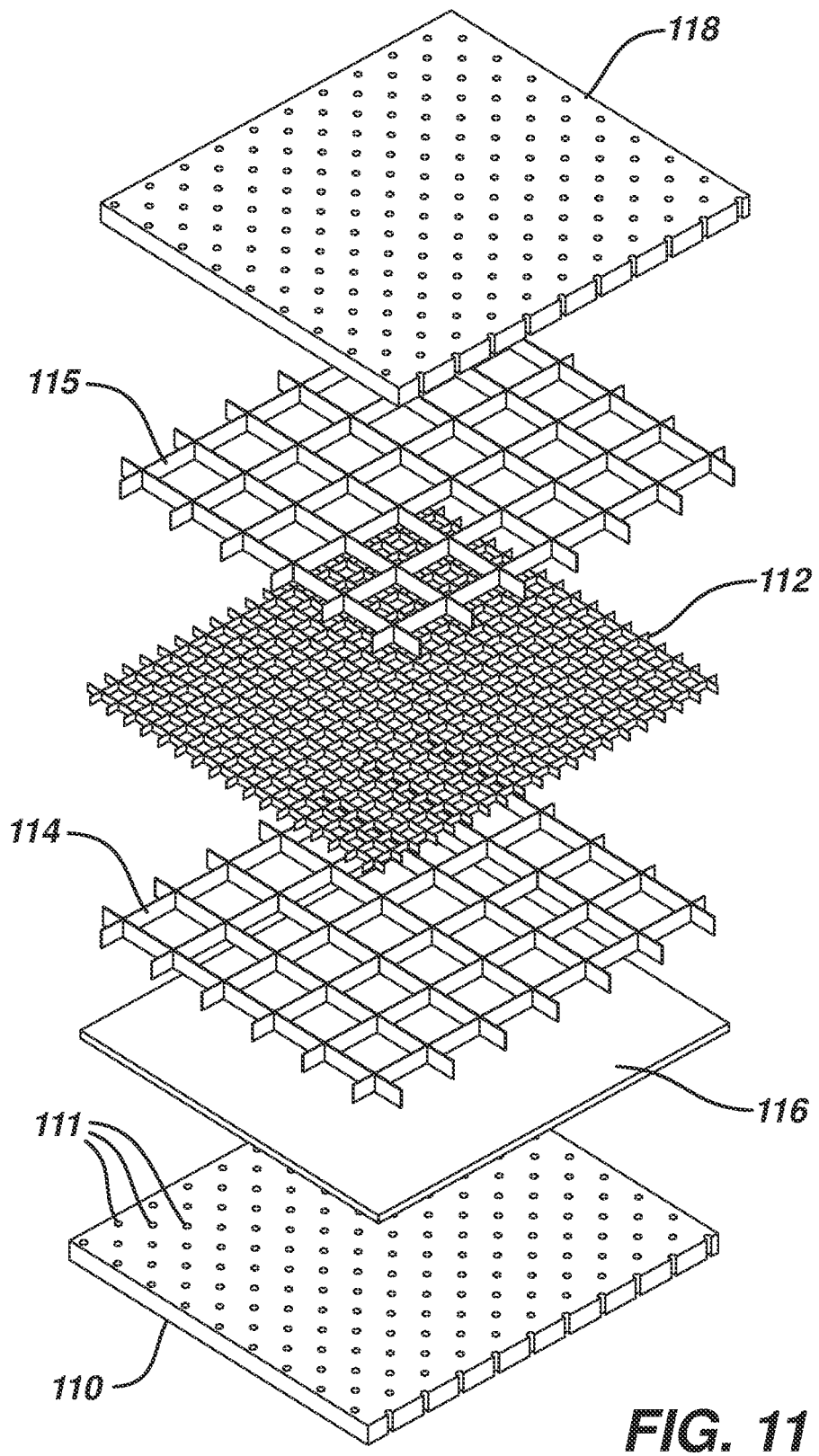

FIG. 1 in part (a) a three-dimensional view of an embodiment of the surgical implant according to the invention and in part (b) an enlarged view of a film piece comprising protrusions of this embodiment, FIG. 2 a three-dimensional view of a variant of the embodiment of FIG. 1, FIG. 3 another embodiment of the surgical implant according to the invention, i.e. in part (a) an enlarged three-dimensional view of a film piece including mushroom-shaped protrusions and in part (b) a plan view of part of the implant, FIG. 4 in parts (a) to (h) three-dimensional representations of several embodiments of protrusions for film pieces of surgical implants according to the invention, FIG. 5 another embodiment of the surgical implant according to the invention, i.e. in part (a) a plan view of part of the film piece pattern of the implant, in part (h) a magnified view of a film piece according to part (a) and in part (c) a three-dimensional view of the film piece of part (b), FIG. 6 another embodiment of the surgical implant according to the invention, i.e. in part (a) a plan view of part of the film piece pattern of the implant, in part (b) a magnified view of a film piece according to part (a) and in part (c) a three-dimensional view of the film piece of part (b), FIG. 7 a schematic illustration of an embodiment of a process of manufacturing a surgical implant according to the invention, see Example 1, FIG. 8 a diagram illustrating a geometric calculation related to the embodiment of the surgical implant according to the invention described in Example 1, FIG. 9 a top view of the embodiment of the surgical implant according to the invention described in Example 3, FIG. 10 a schematic illustration of another embodiment of a process of manufacturing a surgical implant according to the invention, see Example 4, and FIG. 11 a schematic illustration of another embodiment of a process of manufacturing a surgical implant according to the invention, see Example 7, FIG. 1 illustrates a surgical implant 1, which comprises a flexible basic structure designed as a surgical mesh 2 serving as a soft-tissue repair sheet. The face of the mesh 2 pointing upwards in the three-dimensional view of FIG. 1(a) is designated by 3. In the embodiment, the mesh 2 includes pores 4 of a hexagonal shape, which are arranged in a honeycomb pattern.

A plurality of film pieces 6 is attached to face 3 of the mesh 4. In the embodiment, the film pieces 6 do not adhere to each other. Each film piece 6 carries a plurality of solid protrusions 8 emerging from the respective film piece 6 in a direction away from the mesh 2, as is best visible in the magnified view of FIG. 1(b). In the embodiment, the protrusions 8 are rod-like, the angle between the longitudinal axis of each protrusion 8 and the surface of the film piece 6 being about 90°. The film pieces 6 have a hexagonal shape as well, but the area of a film piece 6 is greater than that of a pore 8.

A variant of the surgical implant 1 is shown in FIG. 2 and designated by 10. The surgical implant 10 is basically designed like surgical implant 1 so that for corresponding parts the same reference numerals are used as in FIG. 1. In addition to the implant 1, however, the implant 10 comprises a barrier sheet 12 attached to the opposite face 13 of mesh 2. The barrier sheet 12 is designed as a non-porous film and is to prevent ingrowth of bodily tissue via the opposite face 13 into mesh 2 after implantation of the surgical implant 10. In the embodiment, the barrier sheet 12 is larger than the mesh 2, which results in the presence of margins 14 around mesh 2. The margins 14 may assist the handling of implant 10.

Figure 3A:
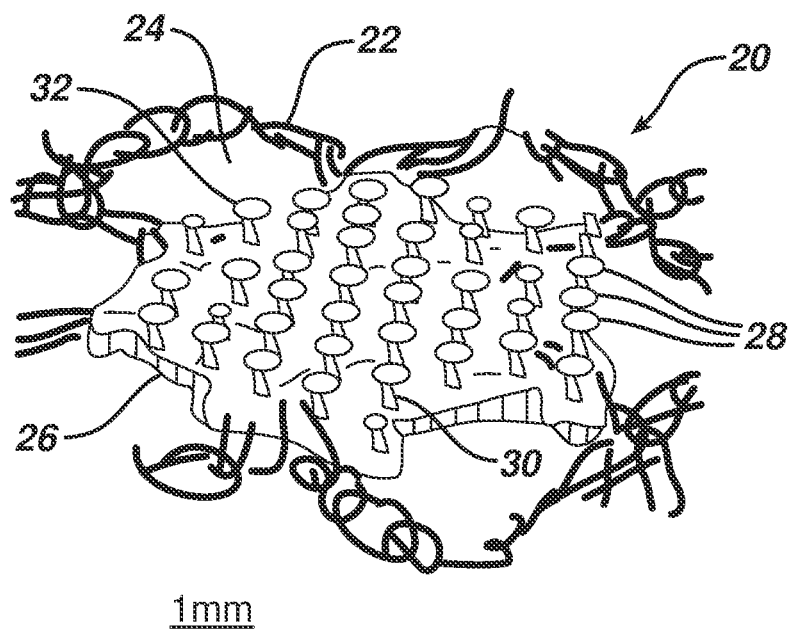
Figure 3B:
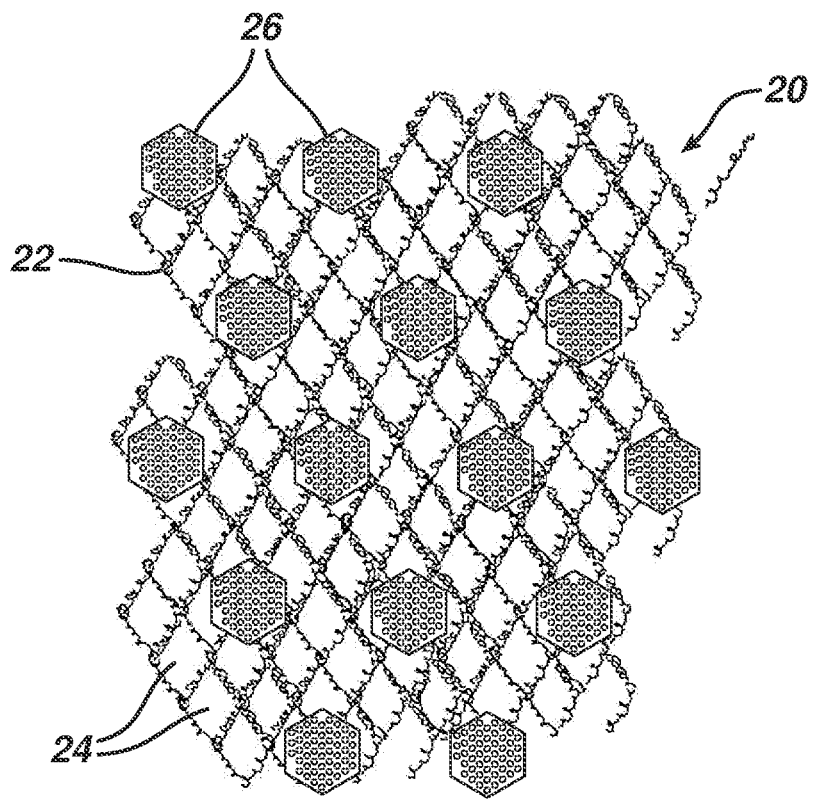

FIG. 3 shows another embodiment of the surgical implant, which is designated by 20 and can be manufactured as described in Example 1 further below FIG. 3(a) is a drawing according to a microscopic picture of a film piece carrying a plurality of protrusions, and FIG. 3(b) is a plan view of part of the implant 20, which, in the embodiment, extends beyond the limits indicated in FIG. 3(b).

The implant 20 comprises a mesh-like basic structure 22 having rhombic pores 24. Its face carries a plurality of hexagonal film pieces 26. The area of each film piece 26 is somewhat larger than the area of one pore 24. A plurality of protrusions 28 emerges from the upper face of each film piece 26. The protrusions 28 are mushroom-like, each protrusion 28 including a stem 30 and a head 32 laterally projecting with respect to the stem 30.

FIG. 3(a) shows that the fibers of the mesh. 22 are almost completely embedded in the material of the film pieces 26.

In the embodiment, the mesh 22 is a commercial "Ultra-pro" mesh of Ethicon, which is a lightweight, monofil, partially resorbable surgical mesh made of fibers of polypropylene (non-resorbable) and "Monocryl" (see above; resorbable) having a pore width of about 2.27 mm in one direction and a pore width of about 3.17 mm in a direction perpendicularly thereto. The film pieces 26 are hexagonal having a width in the range of about 3.7 mm to 4.1 mm. The distance between adjacent film pieces 26 is about 4.4 mm. The film pieces 26 cover about 20% of the area of the face of mesh 22. They extend over crossing points of the pores 24. The film pieces 26 including the protrusions 28 are made of poly-p-dioxanone (PDS), which is resorbable. For further details, see Example 1 below.

FIG. 1, in parts (a) to (h), displays several types of solid protrusions, which are all designated by reference numeral 40. Most of the protrusions 40 comprise a stem 42 (some of them a stem with a pronounced foot section 43) and a head 44, which at least partially projects laterally with respect to the stem 42, see FIGS. 4 (a) to 4(e) and 4(g). Some protrusions include a spike 46 extending beyond the head 44, see FIGS. 4(c), 4(e) and 4(g). The protrusion according FIG. 4(f) is completely designed as a spike. FIG. 4(h) shows a protrusion shaped as a bent rod 48. A particularly advantageous form is like a mushroom, see FIG. 4(d).

Figure 4A:
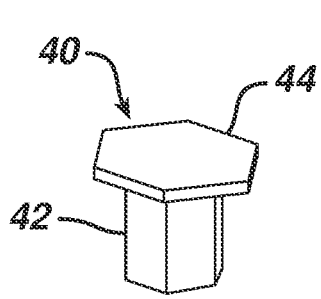
Figure 4B:
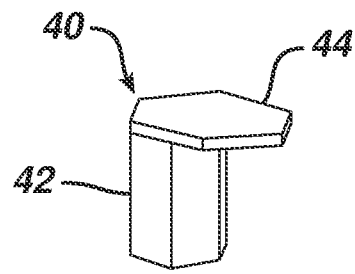
Figure 4C:
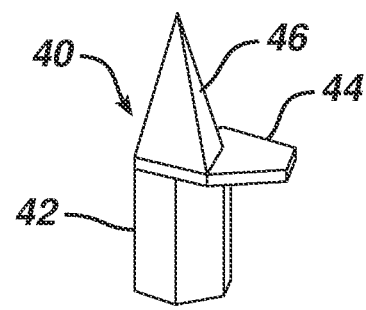
Figure 4D:
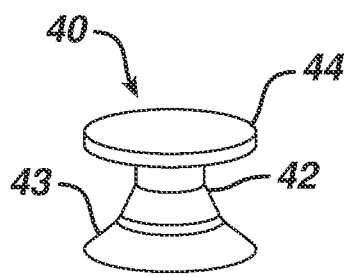
Figure 4E:
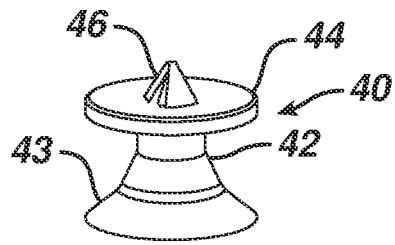
Figure 4F:
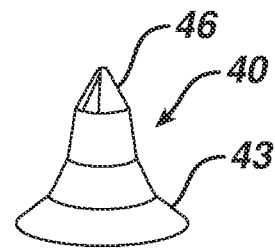
Figure 4G:
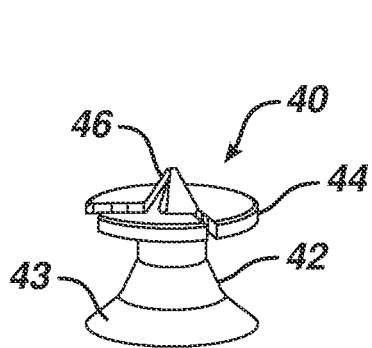
Figure 4H:
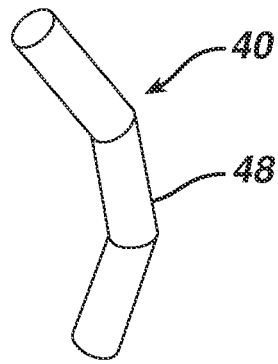

In detail in FIG. 4(a), the stem 42 and the head 44 are hexagonal, with the head. 44 symmetrically projecting laterally with respect to the stem 42. In FIG. 4(b), stem 42 and head 44 are hexagonal, while the head 44 is asymmetrically arranged with respect to the stem 42. In FIG. 4(c), the protrusion is similar to that of FIG. 4(b), but carries a trigonal pyramidal spike. The protrusion of FIG. 4(d) is mushroom-like and has a frusto-conical foot section 43, a tapered middle section of the stem 42 and a relatively flat head 44. In FIG. 4(e), the protrusion is similar to that of FIG. 4(d), but has an additional pyramidal spike. The protrusion of FIG. 4(f) comprises a circular base section 43 with a diameter decreasing down into a sharp tip or spike 46. FIG. 4(g) shows a mushroom-like protrusion similar to that of FIG. 4(e), wherein the head 44 includes some cuts. The protrusion of FIG. 4(h) is shaped as a bent rod 48 made of three straight sections angled with respect to each other; in a variant, it is smoothly bent along its entire length.

Figure 5A:
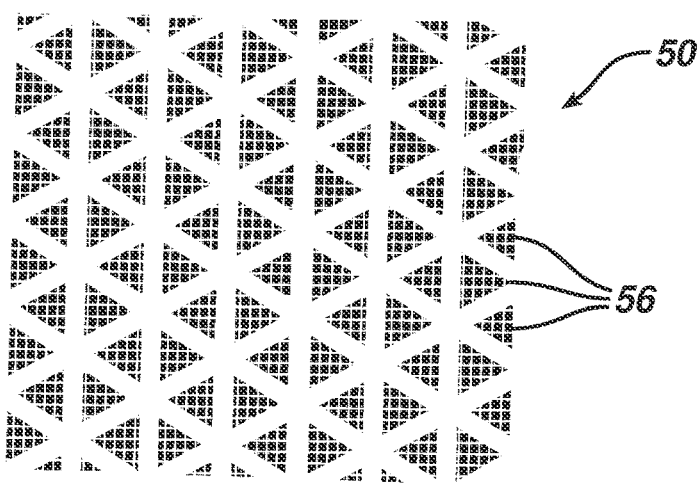
Figure 5B:
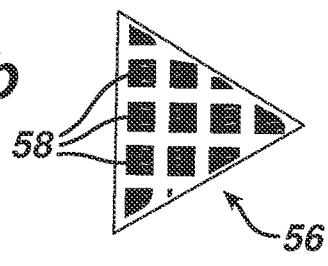
Figure 5C:
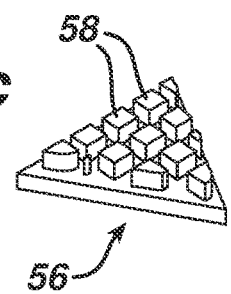

FIG. 5 illustrates another embodiment of the surgical implant, which is designated by 50. In FIG. 5(a), the pattern of film pieces 56 is shown, which have a triangular shape each (see FIG. 5(b)) and comprise essentially cuboidal protrusions (see FIG. 5(c)). The arrangement of the film pieces 56 defines three lines intersecting at respective angles of 60°, which provides for an increased flexibility of the basic structure of the implant 50 in some directions.

Surgical implant 60 shown in FIGS. 6(a) to 6(c) is similar to the implant 50. In this case, however, the distance between film pieces 66 is smaller than that between the film pieces 56, and the protrusions are shaped as longitudinally extending ledges 68.

Some examples follow, which also relate to manufacturing processes of the implant.

Example 1

"UltraPro" Mesh with ~30% in Area Hexagonal PDS Film Pieces with Micro-Protrusions FIG. 7 schematically illustrates an embodiment of a manufacturing process of a surgical implant, i.e. a process of manufacturing the implant 20 already described by means of FIG. 3.

In a first step, a mold 70 containing an array of cavities 71, each cavity having the shape of one protrusion, was made from a 2-component silicone precursor kit (elastomeric kit). To this end, a positive form (master) of polypropylene comprising on one surface 288 mushroom-shaped protrusions/cm$^2$ with a total height of approximately 250 μm, a head diameter of approximately 375 μm, a stem diameter of approximately 200 μm and a foot diameter of approximately 340 μm was used. The liquid silicone elastomer was cast over the polypropylene master and, while keeping a horizontal position, cured at elevated temperatures (50° C. to 80° C.) in an oven for several hours. After cooling to room temperature, the silicone mold, comprising mushroom-shaped negatives of the protrusions, could be removed from the polypropylene master.

As basic structure of the implant, an "UltraPro" mesh (Ethicon) was used (surgical mesh 72 in FIG. 7), which is a composite mesh containing about equal parts of polypropylene fibers and resorbabable "Monocryl" (polyglecaprone) fibers. The mesh could be fixated in a metal frame form to prevent movement and shrinkage.

The mold 70 was placed in a metal form with the cavities 71 facing up, followed by the surgical mesh 72. Next, a hexagonally perforated thin rubber layer (schematically shown as mask 74 in FIG. 7) was placed on top of the mesh 72, followed by a sheet 76 of a material having a lower melting point than the material of the mesh 72. In the example, the sheet was a film of poly-p-dioxanone (PDS) having a thickness of 150 μm. Finally, a plate device 78 (in the example, a soft closed-cell foam material) was placed on top of the sheet 76.

This assembly was placed in a heat press and allowed to heat to a temperature slightly below 130° C. for several minutes under a pressure of about 5 bar. Under these conditions, the poly-p-dioxanone material of sheet 76 got very soft and penetrated the hexagonal openings in the mask 74 and the pores of mesh 72 and filled the cavities 71 in mold 70, thus forming hexagonal film pieces well attached to the mesh and including protrusions. After cooling down the assembly to ambient temperatures (or a temperature below 50° C.), the pressure could be released and the mold 70, the mask 74 and the plate device 78 taken away. Because of its high flexibility, the silicone mold 70 could be removed from the protrusions without problems.

Multiple micro-protrusions were identified under a scanning electron microscope with a total height of about 290 μm, a head width of about 360 μm with a perimeter thickness of about 20 μm, and a stem diameter of about 150 μm to 200 μm.

The resulting surgical implant was flexible and conformable like the basic mesh 72. No remarkable stiffness was introduced. A handling test on a pig stomach showed a good attachment to tissue, like fat or muscle, and at the same time no self-attaching properties compromising the handling during, e.g., rolling or folding.

In detail: A surgical implant manufactured as described in Example 1 and having a size of 7 cm×9 cm exhibited in a bench top test on a pig stomach a good attachment to muscle or fatty tissue, after a slight pressing force had been exerted to the tissue for a short period of time. The shear force (determined with a spring scale) was about 1.1 N. The implant could be easily removed and placed again without losing much attachment force.

The implant could also be easily rolled, passed through a trocar, unrolled in the abdominal cavity and placed against the abdominal wall according to a TAPP procedure. In TAPP the surgeon enters the peritoneal cavity and places a mesh through a peritoneal incision over possible hernia sites. The implant of Example 1 attached well to the tissue, could be easily handled and did not undesirably stick to the bowel during handling.

The total area of all film pieces turned out to be about 30% of the area of the surface of the basic structure (mesh 72). Surprisingly, even such a relatively small total film piece area exhibited a good tissue attachment to muscle and fascia, see above, without negatively compromising the elasticity and flexibility of the implant in a handling test.

The total film piece area was determined by a geometrical calculation, see FIG. 8, assuming the shape of an equilateral hexagon for each film piece and equal sizes for all film pieces a=r=2.065 mm was determined by means of a microscope. Using h=[(½)√3]a, the area A of one hexagon is $$A = 6(½)a[(½)\sqrt{3}]a = 1.5\sqrt{3}a^2 = 11.08 \text{ mm}^2.$$

A rectangular piece of the surgical implant of Example 1 having a size of 60 mm×110 mm contained 8*13=104 film pieces. Thus, the above ratio is 104*11.08/(60*110)=0.175 or 17.5%.

Example 2

"TiGr-Matrix" with ~20% in Area Hexagonal PDS Film Pieces with Micro-Protrusions TiGr-Matrix® by Novus Scientific is a composite mesh made from long- and short-term multifilament absorbable fibers. Fast absorbing fibers consist of a copolymer of glycolide, lactide and trimethylene carbonate and are basically absorbed within 4 months. Long-term absorbing fibers are made from a copolymer of lactide and trimethylene carbonate and are completely absorbed within about 3 years.

A surgical implant was prepared as described in Example 1, but using a 7 cm×11 cm piece of TiGr-Matrix® instead of the "UltraPro" mesh as basic structure. The film pieces were irregularly rounded and were firmly attached to the basic structure.

The resulting implant was only slightly stiffer than the basic structure mesh during handling and could be easily rolled up and unrolled without major mesh-to-mesh self-attachment.

Example 3

Porous cPTFE Sheet Between Circular PDS Film Pieces Having Protrusions on One Side Omyra® mesh by B. Braun is a mesh-like film for hernia repair. It is made of a condensed polytetrafluoroethylene (cPTFE), where star-shaped pores of about 2, 4 mm are cut out to introduce mesh-like properties into the cPTFE film.

Nine film pieces of PDS film (8 mm diameter, thickness about 150 µm) were placed on one face of a 7 cm×7 cm perforated cPTFE patch (Omyra® mesh), the spaces between the film pieces being about 1 cm, 9 similar film pieces were placed on the other face of the patch, just opposite the first film pieces. This assembly was arranged between the silicone mold from example 1 and one non-textured silicon pad from example 1. The whole assembly was placed between two metal plates in a heat press and heated, pressed for about 5 Minutes at about 120° C. and allowed to cool down in the press to ambient temperatures.

In this way, protrusions were formed on the film pieces at one face of the cPTFE patch, whereas these film pieces were firmly fused with the counterpart film pieces at the opposite face of the patch, the patch sheet being embedded in-between. The counterpart film pieces were smooth. The protrusions were easily palpatable with a finger to find the correct face for positioning the implant. Overall characteristics regarding bending during handling were not altered. In the film areas, the cPTFE struts were embedded with about 60 µm PDS film on both sides (in the protrusion-free micro-regions). Total thickness of the PDS film with protrusions was about 560 µm, with mushroom-like micro-protrusions of about 250 µm height, 390 µm width at the heads and 190 µm at the stems. The total film piece area is calculated to be about 10% of the total sheet area.

FIG. 9 shows the surgical implant (designated by 90) prepared in Example 3. It comprises the Omyra® mesh as basic structure 92, which includes reinforcement lines 94, and nine film pieces 96.

Example 4

Tight-Weight PP Mesh with Palpatable Film Pieces

A light-weight polypropylene (PP) mesh having a comparable knitting structure as the UltraPro® mesh available from Ethicon, Inc., Somerville, N.J. U.S.A., used in Example 1, but without the absorbable Monocryl® filaments (polyglecaprone 25) was prepared. This mesh (basic structure) was heat-laminated similar to Example 1, but with a slightly different setup, see FIG. 10.

From bottom to top, the layers are: a silicon mold 100 containing an array of cavities 101, each cavity having the shape of one protrusion, a sheet 106 of PDS for forming the film pieces including the protrusions, a rubber mask 104, the above PP mesh as basic structure 102, and a plan elastic plate device 108 of silicon (without cavities). In this case, protrusions are formed all over the mold 100 and the sheet 106, but the mask 104 shields part of the mesh 102 so that only film pieces (with protrusions) attach to the mesh.

The protrusions of the film pieces were easily palpatable (even with gloves), which enables a side differentiation.

The surgical implant prepared in Example 4 was tested in a rat skin friction model comparable to WO 2006/092236 A1, having a 500 g (5N) pre-load on the rat skin. The maximum friction force was about 13N for a 5 cm×10 cm contact area.

Example 5

Light-Weight PP Mesh with Palpatable Film Pieces on Both Faces

In a first step, the surgical implant of Example 4 was prepared. Afterwards, the PP mesh including the film pieces (with protrusions) was placed between two silicon molds and laminated and cooled down again.

This resulted in a surgical implant comprising a mesh-like basic structure having film pieces with protrusions on both faces. The implant was flexible and could be attached on both sides to tissue or fat structures.

Example 6

Porous cPTFE Sheet Between Rectangular PDS Film Pieces with Protrusions

A 10 cm×10 cm perforated cPTFE patch (Omyra® mesh, B. Braun, as also used in Example 3) was placed together with five film pieces on each side, respective pairs opposing each other, of PDS film (thickness 150 µm, each one 1 cm×1 cm square; four pieces in the corners and one in the center of the patch) between two silicone molds prepared as in Example 1. This assembly was placed between two metal plates in a heat press and heated, pressed for about 5 Minutes at about 120° C. and allowed to cool down in the press to ambient temperatures.

The resulting surgical implant comprised film pieces with protrusions on both faces of the cPTFE patch, the latter being well embedded in the PDS mass of the film pieces.

Example 7

Light-Weight PP Mesh with Film Pieces Having Protrusions on Both Sides

As the basic structure, a light-weight polypropylene (PP) mesh as prepared in Example 4 was used.

FIG. 11 schematically shows the set-up for manufacturing the surgical implant of Example 7. The layers in FIG. 11 are, from bottom to top: a silicon mold 110 containing an array of cavities 111, each cavity having the shape of one protrusion, a sheet 116 of PDS for forming the film pieces including protrusions, a rubber mask 114, the above PP mesh as basic structure 112, another rubber mask 115 and a second mold 118 containing an array of cavities, each cavity having the shape of one protrusion.

In a heat lamination process similar to that of Example 4, the PDS material is pressed into the pores of mesh 112 and the cavities of both molds 110 and 118, whereas the masks 114 and 115 shield the mesh 112 at both sides and define clean borderlines of the film pieces. In this way, the film pieces formed comprise protrusions on both faces and are well attached to the mesh 112.

The appearance of the film pieces was determined under the microscope: A flat film piece area showed a thickness of 240 µm to 290 µm in different areas of the film piece, top protrusions were about 290 µm high and bottom protrusions were about 320 µm high. The mushroom-like protrusions with a head width of about 360 µm and a smallest stem width of about 160 µm were not aligned between both faces. The protrusions were facing away from both mesh faces.

The resulting surgical implant showed fixation properties on both sides to soft tissue like, fat, muscle, or fascia. The implant was not sticking to itself when tightly rolled up and then unrolled, which is important for laparoscopic surgery.

The invention claimed is:
1. A process of manufacturing a surgical implant the implant comprising a flexible basic structure having a face and a plurality of resorbable film pieces attached to the face of the basic structure, wherein each film piece comprises a plurality of protrusions emerging from the respective film piece in a direction way from the basic structure, characterized by the steps of:

providing a mold containing an array of cavities, each cavity having the shape of one protrusion, filling the mold with a fluid material forming the film pieces and the protrusions according to a pattern defining the shapes and locations of the film pieces, hardening the fluid material, attaching the film pieces to a basic structure, with the protrusions pointing away from the basic structure, and removing the mold;

wherein the pattern defining the shapes and locations of the film pieces is determined by a mask placed between the basic structure and the material to be filled in the mold and the process further characterized by the steps of providing a layered assembly comprising, in this order: the mold, a surgical mesh as the basic structure, the mask, a sheet of material for the film pieces having a lower melting point than the surgical mesh, a flexible plate device, heating the sheet of material to a temperature higher than its melting point and lower than the melting point of the surgical mesh, pressing the mold and the plate device towards each other, whereby the material for the film pieces is transferred through the mask into the mold and embeds the surgical mesh, and lowering the temperature and removing the mold.

2. The process according to claim 1, characterized in that the mold is flexible and comprises at least one of the following materials: flexible material, silicone, polyurethane, natural rubbers, synthetic rubbers.

3. The process according to claim 1, characterized in that the flexible plate device has one of the following properties: comprising a closed surface being designed as a second mold, which is flexible and contains an array of cavities, each cavity having the shape of one protrusion.

* * * * *